United States Patent
Weng et al.

(10) Patent No.: US 7,141,179 B2
(45) Date of Patent: Nov. 28, 2006

(54) MONITORING SEMICONDUCTOR WAFER DEFECTS BELOW ONE NANOMETER

(75) Inventors: Wu-An Weng, Hsinchu (TW); Wang-Tsai Hsu, Hsinchu (TW); Kun-Yu Liu, Hsinchu (TW); Yi-Chieh Lai, Hsinchu (TW)

(73) Assignee: Macronix International Co., Ltd., Hsinchu (TW)

( * ) Notice: Subject to any disclaimer, the term of this patent is extended or adjusted under 35 U.S.C. 154(b) by 64 days.

(21) Appl. No.: 10/924,426

(22) Filed: Aug. 23, 2004

(65) Prior Publication Data

US 2006/0037941 A1    Feb. 23, 2006

(51) Int. Cl.
*B44C 1/22* (2006.01)
*G01N 29/00* (2006.01)

(52) U.S. Cl. ............... 216/84; 216/85; 216/96; 216/99; 438/14; 73/781

(58) Field of Classification Search ............ 216/84, 216/85, 96, 99; 438/14; 73/781
See application file for complete search history.

(56) References Cited

U.S. PATENT DOCUMENTS

| 5,764,353 | A | * | 6/1998 | Tate et al. ............. 356/239.8 |
| 6,048,395 | A | * | 4/2000 | Iida et al. ............... 117/20 |
| 6,353,222 | B1 | * | 3/2002 | Dotan .................. 250/310 |
| 6,777,677 | B1 | * | 8/2004 | Nozoe et al. ............ 250/310 |
| 2004/0025983 | A1 | * | 2/2004 | Morita et al. ............ 148/562 |

* cited by examiner

*Primary Examiner*—Shamim Ahmed
(74) *Attorney, Agent, or Firm*—Stout, Uxa, Buyan & Mullins, LLP

(57) ABSTRACT

The invention describes a method to facilitate the use of low-sensitivity monitoring equipment for detecting and monitoring defects on the surface of semiconductor wafers. The method includes the use of a hydrofluoric acid solution for increasing the dimensions of a defect and the application of a thin-film layer of a metal, such as titanium, for improving the appearance of the defect such that the defect dimensions increase to above 0.1 nanometer, the detection threshold for economical low-sensitivity monitoring equipment.

29 Claims, 2 Drawing Sheets

MONITORING SEMICONDUCTOR WAFER DEFECTS BELOW ONE NANOMETER

BACKGROUND OF THE INVENTION

1. Field of the Invention

The present invention relates generally to the field of semiconductor processing and, more particularly, to the monitoring and detection of defects in connection with the fabrication of semiconductor devices.

2. Description of the Prior Art

In the semiconductor industry an important consideration is the yield as a percentage of tested acceptable chips per wafer. This percentage is directly related to the profitability of the manufacturer. One factor influencing the yield is the quality of the raw material, including the density of surface defects (number per $cm^2$). Another factor is the number of surface defects introduced by the manufacturing process (including chemical and mechanical polishing).

Surface defects need to be made visible to assess further treatment for ideally eliminating the defects. The sizes of these defects can be in the range below 0.1 nanometer or 1,000 angstroms (Å). For the detection and monitoring of defects below 0.1 nanometer, high-sensitivity, expensive monitoring equipment may be needed which for example may be more suited for laboratory rather than production applications. It would be desirable to be able to detect defects sized below 0.1 nanometer with commonly used low-sensitivity monitoring equipment.

SUMMARY OF THE INVENTION

The present invention addresses and tends to alleviates the above mentioned deficiencies associated with the prior art. In order to facilitate the use of low-sensitivity monitoring equipment, thus lowering the cost of monitoring for defects, the present invention proposes to efficiently and conveniently enlarge the defect size above the threshold of 0.1 nanometer. This is accomplished by etching for which a hydrofluoric acid solution may be used and a subsequent deposition of a thin-film layer for which titanium may be used, which enhances the appearance of the defect above the 0.1 nanometer threshold of the monitoring capability of low-sensitivity monitoring equipment, thus providing easier and more economical monitoring for semiconductor material defects.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention are apparent in the following detailed description and claims that follow.

DETAILED DESCRIPTION OF THE PRESENTLY PREFERRED EMBODIMENTS

Figure 1:
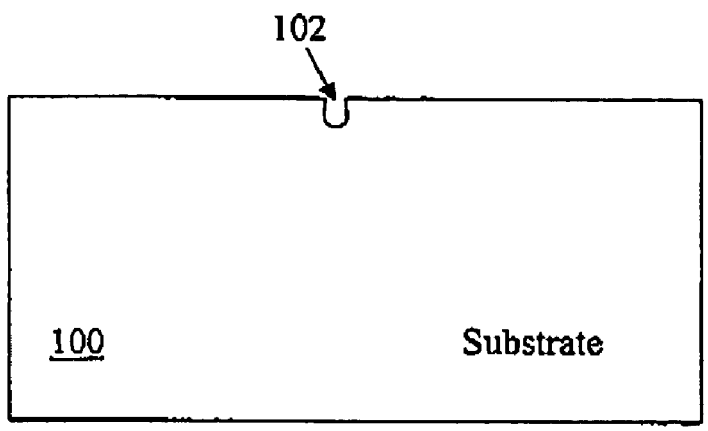
FIG. 1 is a cross-sectional view of a semiconductor wafer with a defect.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. It is to be understood and appreciated that the process steps and structures described herein do not cover a complete process flow for the manufacture of image sensor packages. The present invention may be practiced in conjunction with various integrated circuit fabrication techniques that are conventionally used in the art, and only so much of the commonly practiced structure and process steps are included herein as are necessary to provide an understanding of the present invention.

The present invention provides a method of monitoring defects of a nanometer order, wherein defects (e.g., defects smaller than 0.1 nanometer in size) are increased above 0.1 nanometer in size and enhanced in appearance to facilitate use of low-sensitivity monitoring equipment. The use of such low-sensitivity monitoring equipment, such as optical microscopes that are ubiquitous in wafer fabrication facilities, can be easier and far more economical than the employment of high-sensitivity equipment, such as electron microscopes which can be more expensive in procurement, footprint and operation, thus perhaps being more suitable for use in a laboratory environment.

The present invention proposes to increases the diameter of the defect cavity to above 0.1 nanometer or 1,000 angstroms (Å), which presently is a detection threshold level for low-sensitivity monitoring equipment.

Referring more particularly to the drawings, all the following figures show cross-sections of a substrate, such as a semiconductor wafer. FIG. 1 illustrates one embodiment of the invention applied to the substrate, which as mentioned may comprise a wafer 100. At least one defect 102 of less than 0.1 nanometer diameter is disposed in the wafer 100. In the illustrated embodiment the wafer 100 can comprise a blank wafer. According to the inventive method of monitoring defects of a nanometer order, the wafer 100 may be randomly selected from a lot being monitored. Although presently illustrated with a size smaller than 0.1 nanometer, the defect 102 may also have a size equal to or greater than 0.1 nanometer although it is noted that sizes greater than 0.1 nanometer generally can be detected with low-sensitivity monitoring instruments.

Figure 2:
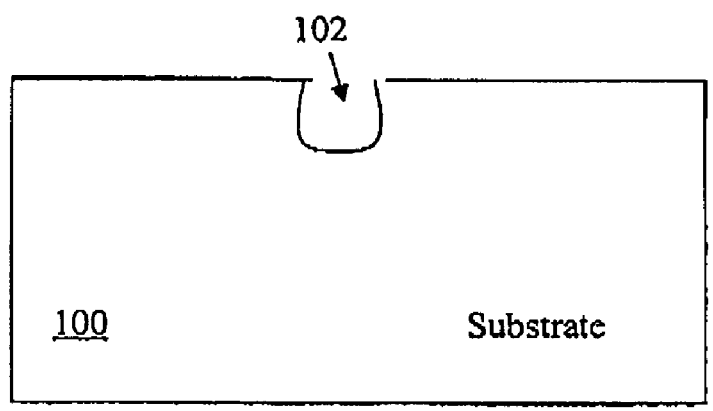
FIG. 2 shows the wafer with the defect after performance of an acid etch.

The wafer 100 is exposed to a treatment, which removes a portion (e.g., a boundary layer) of the wafer and enhances a size of the defect 102. The treatment may comprise an etchant, such as an isotropic etchant. As presently embodied, the treatment is a hydrofluoric (HF) acid solution at a concentration of between 0.01% and 20% by volume, wherein the HF acid solution contacts the wafer 100 for a time between about 10 and about 500 seconds, yielding the structure of FIG. 2. In modified embodiments the HF acid solution may be applied in other ways, such as by spraying, to place a sufficient concentration of HF acid into contact with the defect 102 for a sufficient period of time. While the temperature of the solution may or may not be critical and the above parameters are experimentally determined, an objective is to remove a substrate layer between 1 and 100 nanometer (10 to 1,000 Å) from the wafer surface and the boundary of the defect 102, as seen in FIG. 2. Thus, in keeping with this objective, other etchants, such as other isotropic etchants, may be used as alternatives to or in addition to the HF acid. In an illustrative embodiment, a silicon wafer is immersed in HF acid solution having a temperature of 30 degree C. and a concentration of 2.5% for a period of 120 seconds, to thereby remove a uniform, exposed layer of silicon oxide having a thickness of about 100 Å.

Figure 3:
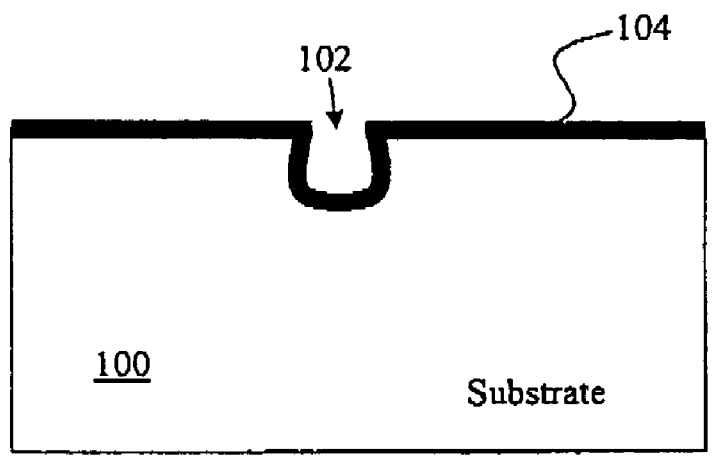
FIG. 3 depicts the wafer after etching and a thin-film layer deposition.

Subsequently, a thin-film layer 104, such as, for example, one or more of a metal, dielectric or polysilicon layer, is deposited to a thickness of about 1 and 50 nanometers (10 to 500 Å) to avoid abnormal coloration of the wafer substrate surface and the defect due to thickness variations which may cause optical thin-film effects. As presently illustrated, the thin-film layer comprises a metal, such as titanium, which is deposited on the wafer surface using a process such as chemical vapor deposition (CVD), as depicted in FIG. 3. The defect can now be readily detected with low-sensitivity monitoring instruments. In an illustrative embodiment, the thin-film layer 104 can comprise a conforming titanium layer having a substantially uniform thickness ranging from about 10 Å to about 500 Å, and in a particular instance having a substantially uniform thickness of, for example, about 150 Å.

Figure 4:
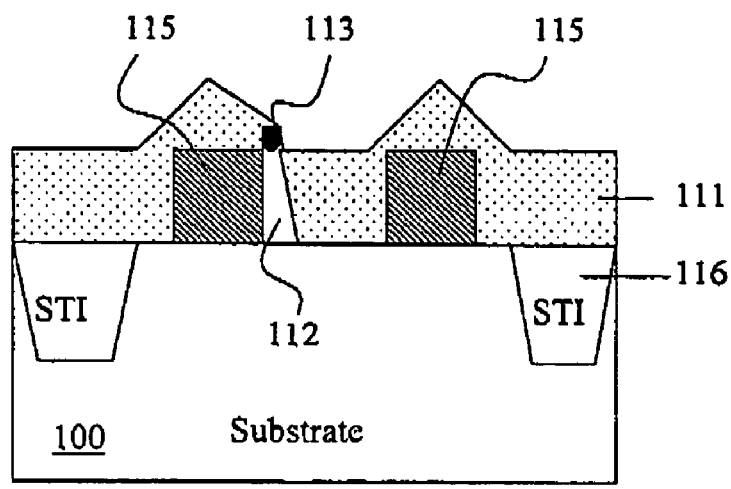
FIG. 4 illustrates a cross-sectional view of a particle-induced defect in a material layer.

In accordance with another embodiment, FIG. 4 shows a wafer 110 carrying a material layer, such as a high-density, plasma generated layer 111 of field oxide covering polysilicon conductors 115. The wafer 110 is shown further comprising shallow trench isolation (STI) structures 116. Field oxide layer 111 comprises a defect 112, caused by an unwanted particle 113 shadowing the deposition of field oxide underneath it. The particle 113 may have a size less than 0.1 microns, the defect 112 may have a dimension at the surface of the field oxide layer 111 less than 0.1 microns, or both. In modified embodiments, either or both dimensions may be equal to or greater than 0.1 microns although as noted above sizes greater than 0.1 nanometer may already be detectable with low-sensitivity monitoring instruments. Typically, when the particle 113 is smaller than 0.1 um it cannot be detected with low-sensitivity monitoring instruments. Consequently, using prior-art techniques, the defect 112 formed under the particle 113 cannot be found and may negatively affect the yield.

According to the illustrated method of monitoring defects of a nanometer order, the wafer 110 may be randomly selected from a lot being monitored. As a first step the particle is removed, which step can be accomplished, for example, by an ion-sputtering process in a vacuum (e.g., in an argon plasma), the molecular equivalent of sand-blasting.

Figure 5:
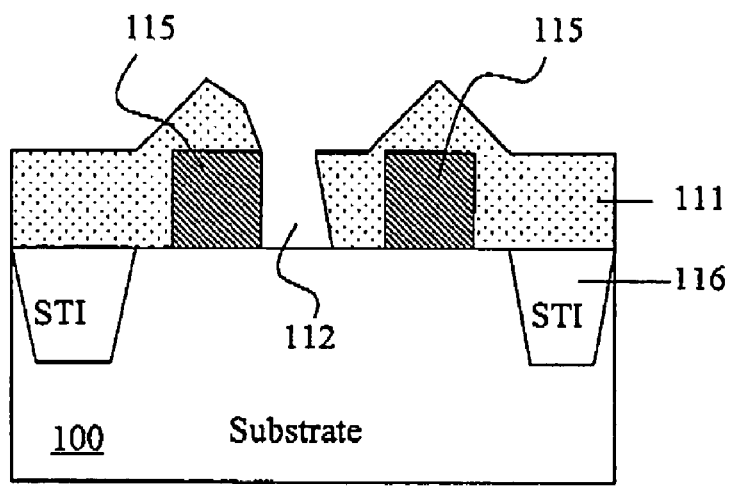
FIG. 5 shows the defect of FIG. 4 after particle removal and performance of an acid etch.

The same HF acid etching as described above with reference to FIG. 2 can then be performed to thereby enhance the dimension of defect 112 above the 0.1 nanometer detection threshold thus generating the structure of FIG. 5. So long as a relatively uniform amount of the field oxide layer 111, between about 1 and 100 nanometer (10 to 1,000 Å) in thickness, is removed from the wafer surface and the boundaries of the defect 102, as seen in FIG. 5, other etchants, such as other isotropic etchants, may be used as alternatives to or in addition to the HF acid solution. The etchants may, in one example, have selectivities which are greater for the field oxide layer 111 than for the wafer 110. In an illustrative embodiment, a silicon wafer is immersed in HF acid solution having a temperature of 30 degree C. and a concentration of 2.5% for a period of 120 seconds, to thereby remove a layer of silicon oxide having a thickness of about 100 Å.

Figure 6:
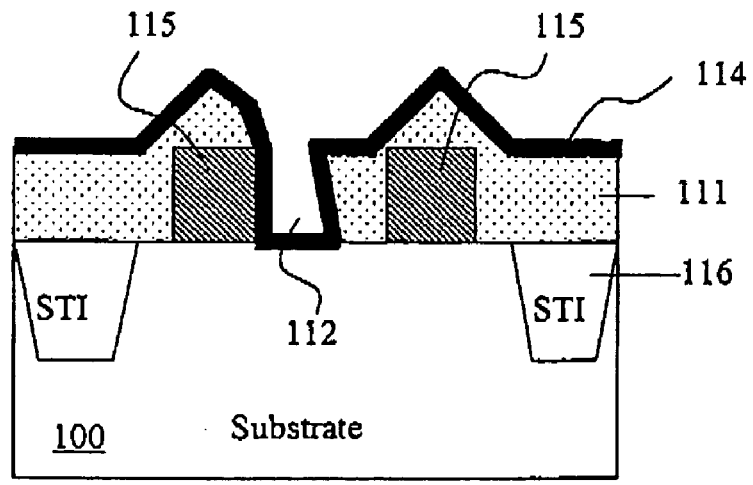
FIG. 6 depict the defect of FIG. 5 after a thin-film layer deposition.

Subsequently, the same thin-film layer deposition as described above in connection with FIG. 3 can be applied to yield the structure shown in FIG. 6, whereby application of thin-film layer 114 (e.g., titanium) prevents coloration of the defect 112 for convenient scanning by low-sensitivity monitoring equipment.

In view of the foregoing, it will be understood by those skilled in the art that the methods of the present invention can facilitate fabrication of image sensor packages. The above-described embodiments have been provided by way of example, and the present invention is not limited to these examples. Multiple variations and modification to the disclosed embodiments will occur, to the extent not mutually exclusive, to those skilled in the art upon consideration of the foregoing description. For example, the use of various processes other than chemical vapor deposition are contemplated. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A method of detecting a defect cavity sized below 0.1 nanometer with commonly used low-sensitivity monitoring equipment, comprising:

a) selecting a wafer from a lot;

b) applying a treatment to the selected wafer, the treatment removing a 1 to 100 nanometer thick portion of the selected wafer and enhancing a size of a defect cavity in the wafer to above 0.1 nanometer; and c) applying a 1 to 50 nanometer thick metallic layer on the treated wafer:

d) scanning the wafer for cavity defects using 0.1 nanometer detection threshold monitoring equipment.

2. The method as set forth in claim 1, wherein the metallic layer is applied over the defect to enhance an appearance of the defect as seen through the monitoring equipment.

3. The method as set forth in claim 1, wherein the treatment comprises use of an etchant.

4. The method as set forth in claim 1, wherein the treatment isotropically etches a surface of the selected wafer.

5. The method as set forth in claim 1, wherein the wafer is randomly selected from the lot.

6. The method as set forth in claim 1, wherein the treatment comprises removal of a layer of about 1 nanometer from an exposed surface of the wafer and a boundary of the defect.

7. The method as set forth in claim 6, wherein the applying of a treatment comprises applying a hydrofluoric acid solution.

8. The method as set forth in claim 1, wherein the treatment comprises removal of a layer of about 0.1 nanometer from an exposed surface of the wafer and a boundary of the defect.

9. The method as set forth in claim 1, wherein:

the metallic layer is applied over the defect to enhance an appearance of the defect as seen through the monitoring equipment.

10. The method as set forth in claim 9, wherein the metallic layer comprises titanium.

11. A method for enhancing a defect cavity, caused by a particle, on a semiconductor wafer carrying a material layer, the method comprising:

a) selecting a wafer from a lot;

b) applying a process to remove the particle;

c) following the process, applying a treatment to enhance a size of the defect cavity on the wafer to above 0.1 nanometer;

d) scanning the wafer for defect cavities using 0.1 nanometer detection threshold monitoring equipment.

12. The method as set forth in claim 11, wherein the material layer comprises field oxide.

13. The method as set forth in claim 11, wherein the scanning is preceded by applying a thin-film layer over the defect to enhance an appearance of the defect as seen through the monitoring equipment.

14. The method as set forth in claim 11, wherein the wafer is randomly selected from the lot.

15. The method as set forth in claim 11, wherein the defect before enhancement is smaller than about 0.1 nanometer.

16. The method as set forth in claim 11, wherein the treatment comprises use of an etchant.

17. The method as set forth in claim 16, wherein the treatment comprises use of a hydrofluoric acid solution.

18. The method as set forth in claim 17, wherein the treatment comprises the removal of a layer of about 1 nanometer from the material layer and from a boundary of the defect.

19. The method as set forth in claim 11, wherein the scanning is preceded by applying a thin-film layer over the defect to enhance an appearance of the defect as seen through the monitoring equipment and the thin-film layer comprises a layer of metal.

20. The method as set forth in claim 19, wherein the metal layer comprises titanium.

21. A method for monitoring a defect cavity in nanometer order, comprising:

a) providing a wafer which may have a defect cavity thereon;

b) applying a chemical treatment to the wafer to enhance a size of the defect cavity to above about 0.1 nanometer;

c) forming a 1 to 50 nanometer thick conformal material layer on the treated wafer; and d) detecting the defect cavity with a low-sensitivity monitoring instrument having a detection threshold of about 0.1 nanometer.

22. The method as set forth in claim 21, wherein the chemical treatment comprises an etching treatment.

23. The method as set forth in claim 22, wherein an etchant of the etching treatment comprises a hydrofluoric (HF) acid solution.

24. The method as set forth in claim 23, wherein a concentration of the HF acid solution is about 0.01%~20%.

25. The method as set forth in claim 21, wherein etching the defect takes about 10~500 seconds.

26. The method as set forth in claim 21, wherein the conformal material layer comprises at least one of a metal layer, a dielectric layer and a polysilicon layer.

27. The method as set forth in claim 26, wherein the metal layer comprises a titanium layer.

28. The method as set forth in claim 21, wherein a thickness of the conformal material layer is about 10~500 angstrom.

29. The method as set forth in claim 11, wherein d) is preceded by applying a 1 to 50 nanometer thick metallic layer on the treated wafer.

* * * * *